(12) United States Patent
Igarashi et al.

(10) Patent No.: US 11,007,378 B2
(45) Date of Patent: May 18, 2021

(54) STERILIZATION APPARATUS

(71) Applicant: Ushio Denki Kabushiki Kaisha, Tokyo (JP)

(72) Inventors: Tatsushi Igarashi, Tokyo (JP); Koichi Kamei, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 82 days.

(21) Appl. No.: 16/074,698

(22) PCT Filed: Jan. 30, 2017

(86) PCT No.: PCT/JP2017/003172
§ 371 (c)(1),
(2) Date: Aug. 1, 2018

(87) PCT Pub. No.: WO2017/135190
PCT Pub. Date: Aug. 10, 2017

(65) Prior Publication Data
US 2019/0038914 A1    Feb. 7, 2019

(30) Foreign Application Priority Data
Feb. 2, 2016    (JP) .............................. JP2016-017843

(51) Int. Cl.
*A61F 9/008*    (2006.01)
*A61N 5/06*    (2006.01)
(Continued)

(52) U.S. Cl.
CPC .......... *A61N 5/0624* (2013.01); *A61L 2/0047* (2013.01); *G02B 5/28* (2013.01);
(Continued)

(58) Field of Classification Search
USPC ......................................................... 607/88
See application file for complete search history.

(56) References Cited

U.S. PATENT DOCUMENTS

2002/0133212 A1*    9/2002    Satoh ................... A61N 5/0616
607/88
2003/0017073 A1    1/2003    Eckhardt et al.
(Continued)

FOREIGN PATENT DOCUMENTS

JP    2004-079281 A    3/2004
JP    2005-023554 A    1/2005
(Continued)

OTHER PUBLICATIONS

International Search Report issued in PCT/JP2017/003172; dated May 9, 2017.
(Continued)

*Primary Examiner* — Michael W Kahelin
*Assistant Examiner* — George E Banis
(74) *Attorney, Agent, or Firm* — Studebaker & Brackett PC

(57) ABSTRACT

Disclosed is a sterilization apparatus that can kill or inactivate sterilization target organisms present on a body or in the body without damage to human cells and has high energy efficiency. A sterilization apparatus is configured to irradiate a sterilization target organism on a body or in the body with light and thereby killing or inactivating the sterilization target organism. The sterilization apparatus includes: a light source configured to emit light having wavelengths within a wavelength range of 190 nm to 230 nm and a wavelength range of 230 to 300 nm; a power supply unit configured to supply power to the light source; a control unit configured to control the power supply unit; and an optical filter. The power supply unit is controlled by the control unit so that an irradiation amount of light having a wavelength within the wavelength range of 230 to 300 nm in one light irradiation is not more than 9 mJ/cm$^2$.

19 Claims, 3 Drawing Sheets

(51) Int. Cl.
*G02B 5/28* (2006.01)
*A61L 2/00* (2006.01)

(52) U.S. Cl.
CPC ......... *A61L 2202/14* (2013.01); *A61N 5/0616* (2013.01); *A61N 2005/0654* (2013.01); *A61N 2005/0661* (2013.01); *A61N 2005/0667* (2013.01)

(56) References Cited

U.S. PATENT DOCUMENTS

| | | | |
|---|---|---|---|
| 2003/0018373 | A1 | 1/2003 | Eckhardt et al. |
| 2003/0031586 | A1 | 2/2003 | Eckhardt et al. |
| 2004/0034398 | A1 | 2/2004 | Eckhardt et al. |
| 2014/0131595 | A1* | 5/2014 | Nathan ................ A61L 2/0047 250/504 R |
| 2015/0073396 | A1* | 3/2015 | Randers-Pehrson ......................... A61N 5/0624 606/3 |
| 2016/0107000 | A1* | 4/2016 | Randers-Pehrson ... A61B 18/18 607/88 |

FOREIGN PATENT DOCUMENTS

| | | |
|---|---|---|
| JP | 2005-508664 A | 4/2005 |
| JP | 2009-187043 A | 8/2009 |
| JP | 2014-508612 A | 4/2014 |

OTHER PUBLICATIONS

Yoshiaki Satoh, "Skin type and Photoaging", Aesthetic Dermatology Series, 1991, pp. 35-41, No. 3, Japan.

F. R. De Gruijl et al., "Estimate of the Wavelength Dependency of Ultraviolet Carcinogenesis in Humans and its Relevance to the Risk Assessment of a Stratospheric Ozone Depletion", Health Physics, Oct. 1994, vol. 67, No. 4, pp. 319-325.

* cited by examiner

STERILIZATION APPARATUS

TECHNICAL FIELD

The present invention relates to a sterilization apparatus using ultraviolet rays, and more particularly to a sterilization apparatus applicable to sterilization of harmful organisms present in/on a human body.

BACKGROUND ART

Sterilization, disinfection and the like using ultraviolet rays (hereinafter, referred to simply as "UV sterilization") have conventionally been used in various fields including food and medical fields. UV sterilization is performed by applying ultraviolet rays to DNA in cells of sterilization target organisms (such as bacteria). Specifically, ultraviolet rays are made to be absorbed by DNA in cells to destroy the genetic code of DNA and prevent normal proliferation and metabolism of the cells, whereby the sterilization target organisms including the cells are inactivated.

In UV sterilization, the genetic code of DNA in cells is destroyed as described above. Unlike inactivation (such as sterilization and disinfection) of target organisms by chemicals, sterilization target organisms therefore will not acquire a resistance to ultraviolet irradiation. Unlike chemical-based sterilization, disinfection, or the like, UV sterilization also has an advantage that no chemical or the like remains on the area where the sterilization target organisms are.

UV sterilization is typically applied to organisms (sterilization target organisms) harmful to a human body that are present other than in/on a human body. Examples include surface sterilization of human body-contacting medical instruments (such as a surgical knife and a dental treatment tool) and the like, liquid sterilization targeted for bacteria in water or a solution and air sterilization for killing bacteria present in the air.

Since UV sterilization is extremely effective, there is a high demand for UV sterilization of harmful organisms present on the surface and the like of a human body. For example, to prevent surgical site infection (SSI) which leads to deteriorated hospital readmission rates and death rates, UV irradiation of surgical sites of a human body is considered to be effective. There are also high expectations for UV sterilization in preventing infectious diseases at the sites of wounds, burns, bedsores and the like and at skin implantation sites, and in disinfecting healthy skin, etc.

However, as described above, UV sterilization is performed by destroying the genetic code of DNA in biological cells. If a human body is irradiated with the ultraviolet rays, normal cells of the human body are also damaged as a matter of course. This results in serious troubles in the human body, including photoaging and the occurrence of skin cancer.

From such a reason, UV sterilization has not been widely used as a technique for killing harmful organisms present on/in a human body.

In view of the circumstances, a sterilization apparatus for selectively killing bacteria, or sterilization target organisms, present in a sterilization target site by ultraviolet irradiation without damage to human cells has been proposed in recent years (see Patent Literature 1).

This sterilization apparatus includes a light source that radiates light at least having a wavelength within the wavelength range of approximately 190 to 230 nm, and an optical filter that cuts off light having a wavelength outside the wavelength range of approximately 190 to 230 nm in the light from the light source.

Since such a sterilization apparatus is capable of selective irradiation with only the light within the wavelength range of approximately 190 to 230 nm, the sterilization and disinfection of sterilization target organisms present in a sterilization target site of the body can be performed while substantially avoiding damage to human cells.

CITATION LIST

Patent Literature

Patent Literature 1: Japanese Translation of PCT Patent Application Publication No. 2014-508612

SUMMARY OF INVENTION

Technical Problem

However, the foregoing sterilization apparatus was found to have the following problems.

In the foregoing sterilization apparatus, suppose that light in wavelength ranges other than 190 to 230 nm in the light emitted from the light source, such as a KrCl excimer lamp, is fully cut off by the optical filter, or equivalently, an optical filter that reduces the intensity of transmitted light having a wavelength within the wavelength ranges other than 190 to 230 nm to zero is used. In such a case, the light having a wavelength within the wavelength range of 190 to 230 nm is also considerably attenuated. To irradiate the sterilization target site with a predetermined irradiation amount, e.g., not less than 100 mJ/cm$^2$ of light having a wavelength within the wavelength range of 190 to 230 nm, considerably high power therefore needs to be supplied to the KrCl excimer lamp. A sterilization apparatus having high energy efficiency is thus difficult to configure. There is also a problem that the entire apparatus increases in size since a large-sized power supply unit is needed to supply high power to the KrCl lamp.

The present invention has been made in view of the foregoing circumstances and has as its object the provision of a sterilization apparatus that can kill or inactivate sterilization target organisms present on a body or in the body without damage to human cells and has high energy efficiency.

Solution to Problem

To solve the foregoing problems, the inventors have made intensive study and found that even if the irradiating ultraviolet rays include light outside the wavelength range of 190 to 230 nm, specifically, light within the wavelength range of 230 to 300 nm, the dose of the light within the wavelength range of 230 to 300 nm can be controlled to kill or inactivate sterilization target organisms without damage to human cells, and on the basis of the findings, completed the present invention.

A sterilization apparatus according to the present invention is a sterilization apparatus configured to irradiate a sterilization target organism on a body or in the body with light and thereby killing or inactivating the sterilization target organism, the sterilization apparatus including:

a light source configured to emit light having wavelengths within a wavelength range of 190 nm to 230 nm and a wavelength range of 230 to 300 nm;

a power supply unit configured to supply power to the light source;

a control unit configured to control the power supply unit; and an optical filter, wherein
the power supply unit is controlled by the control unit so that an irradiation amount of light having a wavelength within the wavelength range of 230 to 300 nm in one light irradiation is not more than 9 mJ/cm$^2$.

In the sterilization apparatus according to the present invention, the optical filter may preferably have performance satisfying the following expression (1):

$$0 < fb/fa < 0.09 \times (a_0/b_0), \qquad \text{Exp. (1)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

In the sterilization apparatus according to the present invention, the power supply unit may preferably be controlled by the control unit so that the irradiation amount of light having a wavelength within the wavelength range of 230 to 300 nm in one light irradiation is not more than 4 mJ/cm$^2$.

In such a sterilization apparatus, the optical filter may preferably have performance satisfying the following expression (2):

$$0 < fb/fa < 0.04 \times (a_0/b_0), \qquad \text{Exp. (2)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

In the sterilization apparatus according to the present invention, if the light source is a KrCl excimer lamp,
the optical filter may preferably have performance satisfying the following expression (3):

$$0 < fb/fa < 0.577, \qquad \text{Exp. (3)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

In the sterilization apparatus according to the present invention, if the light source is a KrCl excimer lamp and the power supply unit is controlled by the control unit so that the irradiation amount of light having a wavelength within the wavelength range of 230 to 300 nm in one light irradiation is not more than 4 mJ/cm$^2$,
the optical filter may preferably have performance satisfying the following expression (4):

$$0 < fb/fa < 0.256, \qquad \text{Exp. (4)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

The sterilization apparatus according to the present invention, if the light source is a KrBr excimer lamp,
the optical filter may preferably have performance satisfying the following expression (5):

$$0 < fb/fa < 0.336, \qquad \text{Exp. (5)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

The sterilization apparatus according to the present invention, if the light source is a KrBr excimer lamp and the power supply unit is controlled by the control unit so that the irradiation amount of light having a wavelength within the wavelength range of 230 to 300 nm in one light irradiation is not more than 4 mJ/cm$^2$,
the optical filter may preferably have performance satisfying the following expression (6):

$$0 < fb/fa < 0.149, \qquad \text{Exp. (6)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

In the sterilization apparatus according to the present invention, the optical filter may preferably have performance satisfying the following expression (7):

$$0 < fb/fa < (x/100) \times (a_0/b_0), \qquad \text{Exp. (7)}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/a$_0$, fb=b/b$_0$, and x is the irradiation amount of light having a wavelength within the wavelength range of 230 to 300 nm.

In the sterilization apparatus according to the present invention, the light source may be an LED using a nitride semiconductor.

The optical filter may preferably include a dielectric multilayer film including an SiO$_2$ film and an MgF$_2$ film.

Advantageous Effects of Invention

According to the sterilization apparatus of the present invention, the power supply unit is controlled by the control unit so that the irradiation amount of light having a wavelength within the wavelength range of 230 to 300 nm in one light irradiation is not more than 9 mJ/cm$^2$. This can kill or inactivate sterilization target organisms present on a body or in the body while suppressing damage to human cells.

Since the optical filter does not need to fully cut off the light having a wavelength within the wavelength range of 230 to 300 nm, an optical filter highly transparent to light having a wavelength within the wavelength range of 190 to 230 nm can be used. Since high power does not need to be supplied to the light source, high energy efficiency is obtained.

DESCRIPTION OF EMBODIMENTS

Figure 1:
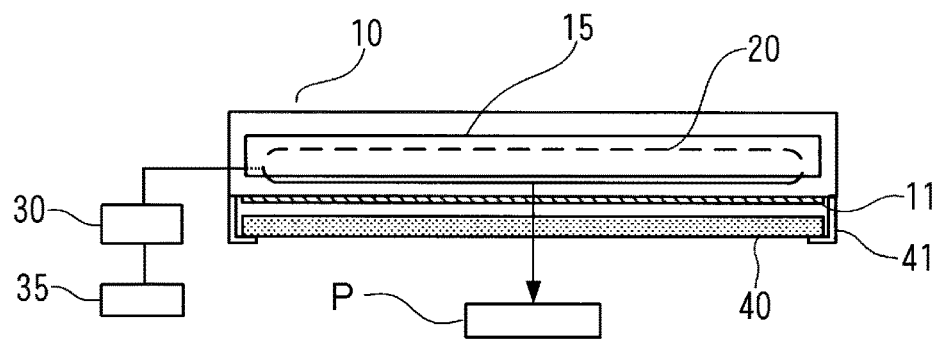
FIG. 1 is an explanatory diagram illustrating a configuration according to an example of a sterilization apparatus of the present invention.

FIG. 1 is an explanatory diagram illustrating a configuration according to an example of a sterilization apparatus of the present invention.

This sterilization apparatus includes a casing 10 having a rectangular solid outer shape. An ultraviolet transmission window portion 11 of rectangular plate shape which is made of, e.g., synthetic quartz glass and transmits ultraviolet rays is provided on a surface (in FIG. 1, lower surface) of this casing 10.

In the casing 10, a rod-shaped excimer lamp 20 serving as a light source is arranged to be opposed to the ultraviolet transmission window portion 11. A gutter-shaped reflecting mirror 15 for reflecting the light from the excimer lamp 20 toward the ultraviolet transmission window portion 11 is arranged behind the excimer lamp 20 in the casing 10 so as to surround the excimer lamp 20.

Oxygen in the air absorbs light having a wavelength of not more than 200 nm. To prevent intensity attenuation of the light from the excimer lamp 20, the interior of the casing 10 is purged with inert gas, such as nitrogen (N$_2$) gas, according to need.

A power supply unit 30 configured to supply power to the excimer lamp 20 is electrically connected to the excimer lamp 20. A control unit 35 configured to control the power supply unit 30 is electrically connected to the power supply unit 30.

An optical filter 40 of rectangular plate shape is arranged outside the casing 10, at a position opposed to the ultraviolet transmission window portion 11. This optical filter 40 is fixed to the casing 10 by a fixing member 41.

In the foregoing sterilization apparatus, the light from the excimer lamp 20 is emitted out of the casing 10 through the ultraviolet transmission window portion 11 to irradiate a sterilization target portion P via the optical filter 40. Sterilization target organisms, such as bacteria, present on the sterilization target portion P are thereby killed or inactivated.

An excimer lamp having an emission light center wavelength of 190 to 230 nm may be used as the excimer lamp 20.

Specific examples of such an excimer lamp 20 include a KrCl excimer lamp having an emission light center wavelength of 222 nm and a KrBr excimer lamp having an emission light center wavelength of 207 nm.

Figure 2:
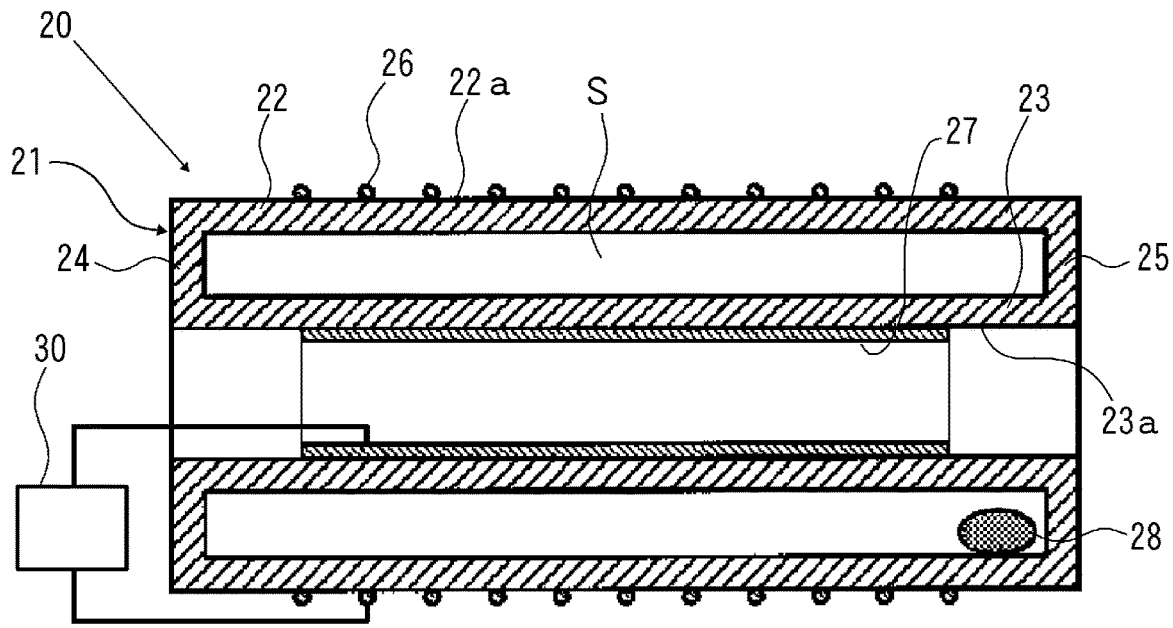
FIG. 2 is an explanatory sectional view illustrating a configuration according to an example of a KrCl excimer lamp.

FIG. 2 is an explanatory sectional view illustrating a configuration according to an example of the excimer lamp 20. In this excimer lamp 20, there is provided an enclosed discharge container 21 including one cylindrical wall member 22 made of a dielectric and the other cylindrical wall member 23 made of a dielectric. The other cylindrical wall member 23 is arranged inside the one cylindrical wall member 22 along the cylinder axis thereof and has an outer diameter smaller than the inner diameter of the one wall member 22. In this discharge container 21, the one wall member 22 and the other wall member 23 are joined by sealing wall portions 24 and 25 at both ends each, so that a cylindrical discharge space S is formed between the one wall member 22 and the other wall member 23. For example, quartz glass may be used as the dielectric constituting the discharge container 21.

One electrode 26 of mesh shape, made of a conductive material such as a metal mesh, is provided on the one wall member 22 of the discharge container 21 so as to be in close contact with an outer peripheral surface 22a thereof. The other electrode 27 of film shape, made of aluminum, is provided on the other wall member 23 of the discharge container 21 so as to cover an outer surface 23a thereof. The one electrode 26 and the other electrode 27 are each electrically connected to the power supply unit 30.

The discharge container 21 is filled with a discharging gas including a mixture of krypton and chlorine or bromine. A light emitting element replenishment material 28 made of a metal chloride or metal bromide is arranged in the discharge container 21.

In this excimer lamp 20, when a high frequency voltage is applied across the one electrode 26 and the other electrode 27, a dielectric barrier discharge occurs in the discharge space S in the discharge container 21. This generates an excimer of the krypton element and the chlorine element or bromine element in the discharge container 21, and excimer light emitted from the excimer is emitted outside from the meshes of the one electrode 26 via the one wall member 22.

Figure 3:
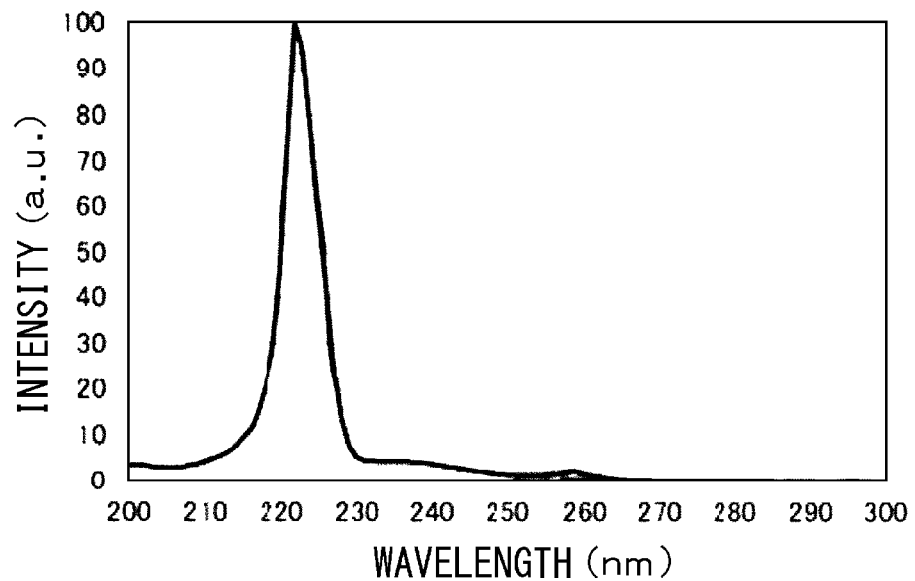
FIG. 3 is a graph illustrating a spectral distribution curve of excimer light emitted from the KrCl excimer lamp.

If the excimer lamp 20 is a KrCl excimer lamp, the excimer light emitted from the excimer lamp 20 has a center wavelength of 222 nm, for example, and includes light having a wavelength within the wavelength range of 230 to 300 nm. FIG. 3 illustrates a spectral distribution curve of the excimer light emitted from the excimer lamp 20.

If the excimer lamp 20 is a KrBr excimer lamp, the excimer light emitted from the excimer lamp 20 has a center wavelength of 207 nm, for example, and includes light having a wavelength within the wavelength range of 230 to 300 nm.

In the sterilization apparatus according to the present invention, the power supply unit 30 is controlled by the control unit 35 so that the irradiation amount of the light having a wavelength within the wavelength range of 230 to 300 nm in one light irradiation is not more than 9 mJ/cm$^2$, preferably not more than 4 mJ/cm$^2$.

A reason why the irradiation amount of the light having a wavelength within the wavelength range of 230 to 300 nm is defined to be the foregoing value will be described below.

Skin cancer occurring when human skin is irradiated with ultraviolet rays is caused as a result of damage to DNA of the skin cells from the ultraviolet rays. For example, if the skin is irradiated with ultraviolet rays in a wavelength range including a wavelength of 260 nm, bases constituting DNA in the skin cells are excited. In the process of returning to the ground state, the bases react with each other to generate dimer molecules such as cyclobutane pyrimidine dimer (CPD) and 6-4PP. Such damage to DNA causes a change in the DNA structure, whereby DNA replication and RNA transcription are hindered to cause skin cancer.

In such ultraviolet-based generation of skin cancer, the irradiation amount (dose) of ultraviolet rays dependent on the wavelength of the ultraviolet rays is known to have a threshold.

Now, continuous exposure to ultraviolet rays included in sunlight causes a change in skin, such as erythema. More specifically, if skin is irradiated with the ultraviolet rays, erythema occurs according to the irradiation amount of the ultraviolet rays. Ultraviolet irradiation of skin has recently been used for a treatment of autoimmune diseases such as vitiligo occurring in the skin. Here, to avoid the risk of developing a skin disease by the ultraviolet irradiation, the irradiation amount of the ultraviolet rays is usually set below the value of minimal erythema dose (MED) which is the lowest irradiation amount of ultraviolet rays at which erythema occurs in the skin.

The wavelengths to cause erythema in the skin are known to be similar to those inducing carcinogenesis (see F. R. deGruijl,: Health Phys. 67 (4): 319-325; 199424 (2001)).

Consequently, as for light having a wavelength within the wavelength range of 230 to 300 nm, damage to human cells can be substantially avoided by setting the irradiation amount in consideration of the MED. Specifically, the MED of light having a wavelength within the wavelength range of 250 to 300 nm is greater than 9 mJ/cm$^2$ in value (see Aesthetic Dermatol, No3, 35 (1991)). Damage to human cells is therefore substantially avoided by setting the irradiation amount of light having a wavelength within the wavelength range of 230 to 300 nm to not more than 9 mJ/cm$^2$.

The foregoing MED is one representing an average value for Japanese people, with respect to light having a wavelength within the wavelength range of 250 to 300 nm. According to the World Health Organization (WHO) Photo Skin Type classifications which express the degrees of sensitivity of skin to ultraviolet rays, the Japanese applies to Type II to Type IV. In consideration of people who belong to Type I, the irradiation amount of light having a wavelength within the wavelength range of 230 to 300 nm may preferably be not more than 4 mJ/cm$^2$.

In UV sterilization, the irradiation amount of light having a wavelength within the wavelength range of 190 to 230 nm in one light irradiation may preferably be not less than 100 mJ/cm$^2$.

The optical filter 40 is constituted by forming a dielectric multilayer film including SiO$_2$ films and MgF$_2$ films on both sides of a substrate made of synthetic quartz glass.

For such an optical filter 40, one having performance satisfying the following expression (1) may preferably be used:

$$0 < fb/fa < 0.09 \times (a_0/b_0), \qquad \text{Exp. (1)}$$

where $a_0$ is the cumulative spectral intensity of light having wavelengths within the wavelength range of 190 to 230 nm and $b_0$ is the cumulative spectral intensity of light having wavelengths within the wavelength range of 230 to 300 nm in the light emitted from the light source, a is the cumulative spectral intensity of light having wavelengths within the wavelength range of 190 to 230 nm and b is the cumulative spectral intensity of light having wavelengths within the wavelength range of 230 to 300 nm in transmitted light when the light emitted from the light source is transmitted through the optical filter 40, fa=a/a$_0$, and fb=b/b$_0$.

If the power supply unit 30 is controlled so that the irradiation amount of light having a wavelength within the wavelength range of 230 to 300 nm in one light irradiation is not more than 4 mJ/cm$^2$, an optical filter having performance satisfying the following expression (2) may preferably be used as the optical filter 40:

$$0 < fb/fa < 0.04 \times (a_0/b_0). \qquad \text{Exp. (2)}$$

If a KrCl excimer lamp is used as the excimer lamp 20 serving as the light source, an optical filter having performance satisfying the following expression (3) may preferably be used as the optical filter 40. If the power supply unit 30 is controlled so that the irradiation amount of light having a wavelength within the wavelength range of 230 to 300 nm in one light irradiation is not more than 4 mJ/cm$^2$, an optical filter having performance satisfying the following expression (4) may preferably be used:

$$0 < fb/fa < 0.577, \qquad \text{Exp. (3)}$$

$$0 < fb/fa < 0.256. \qquad \text{Exp. (4)}$$

If a KrBr excimer lamp is used as the excimer lamp 20 serving as the light source, an optical filter having performance satisfying the following expression (5) may preferably be used as the optical filter 40. If the power supply unit 30 is controlled so that the irradiation amount of light having a wavelength within the wavelength range of 230 to 300 nm in one light irradiation is not more than 4 mJ/cm$^2$, an optical filter having performance satisfying the following expression (6) may preferably be used:

$$0 < fb/fa < 0.336, \qquad \text{Exp. (5)}$$

$$0 < fb/fa < 0.149. \qquad \text{Exp. (6)}$$

By using the optical filter 40 satisfying such performance, the irradiation amount of light having a wavelength within the wavelength range of 190 to 230 nm can be made to be not less than 100 mJ/cm². The foregoing performance required of the optical filter 40 will be described below by using specific examples.

A KrCl excimer lamp was prepared as the light source. The light emitted from this KrCl excimer lamp has a ratio ($a_0/b_0$) of 6.41 between the cumulative spectral intensity ($a_0$) of light having a wavelength within the wavelength range of 190 to 230 nm and the cumulative spectral intensity ($b_0$) of light having a wavelength within the wavelength range of 230 to 300 nm.

Substituting the value of the ratio ($a_0/b_0$) about the foregoing KrCl excimer lamp into the foregoing expression (1) yields a value of 0.577 on the right-hand side, whereby the foregoing expression (3) is derived.

Substituting the value of the ratio ($a_0/b_0$) about the foregoing KrCl excimer lamp into the foregoing expression (2) yields a value of 0.256 on the right-hand side, whereby the foregoing expression (4) is derived.

An optical filter (1) and an optical filter (2) having the following performance with respect to the foregoing KrCl excimer lamp were fabricated:
Optical Filter (1):
fa=0.447, fb=0.145 (fb/fa=0.324)
Optical Filter (2):
fa=0.229, fb=0.030 (fb/fa=0.131)

The foregoing optical filter (1) and the foregoing optical filter (2) are each formed by forming a dielectric multilayer film including $SiO_2$ films and $MgF_2$ films on both sides of a substrate made of synthetic quartz glass. The number of layers of the dielectric multilayer film formed on one side of the substrate is 84. The number of layers of the dielectric multilayer film formed on the other side of the substrate is 86.

The foregoing optical filter (1) satisfies the foregoing expressions (1) and (3). The foregoing optical filter (2) satisfies the foregoing expressions (2) and (4).

A ratio (a/b) between the cumulative spectral intensity (a) of light having a wavelength within the wavelength range of 190 to 230 nm and the cumulative spectral intensity (b) of light having a wavelength within the wavelength range of 230 to 300 nm in the transmitted light when the light emitted from the KrCl excimer lamp is transmitted through the optical filter (1) is determined as follows:

$$a_0/b_0 = 6.41$$
$$fb/fa = 0.324$$
$$a = a_0 \times fa$$
$$b = b_0 \times fb$$

and thus $$a/b = (a_0 \times fa)/(b_0 \times fb)$$
$$= (a_0/b_0)/(fb/fa)$$
$$= 6.41/0.324$$
$$= 19.8.$$

The ratio (a/b) between the cumulative spectral intensity (a) of light having a wavelength within the wavelength range of 190 to 230 nm and the cumulative spectral intensity (b) of light having a wavelength within the wavelength range of 230 to 300 nm in the transmitted light when the light emitted from the KrCl excimer lamp is transmitted through the optical filter (2) is determined as follows:

$$a_0/b_0 = 6.41$$
$$fb/fa = 0.131$$
$$a = a_0 \times fa$$
$$b = b_0 \times fb$$

and thus $$a/b = (a_0 \times fa)/(b_0 \times fb)$$
$$= (a_0/b_0)/(fb/fa)$$
$$= 6.41/0.131$$
$$= 48.9.$$

Figure 4:
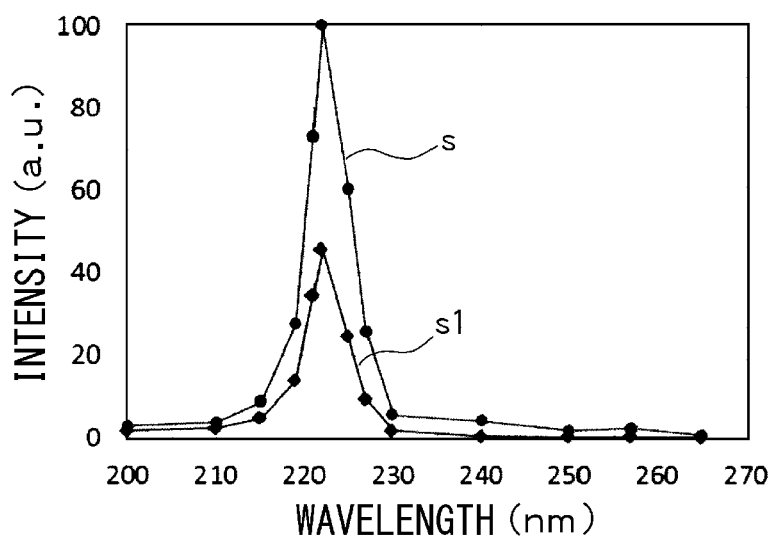
FIG. 4 is a graph illustrating a spectral intensity distribution of the light emitted from the KrCl excimer lamp and a spectral intensity distribution of transmitted light when the light emitted from the KrCl excimer lamp is transmitted through an optical filter (1).
Figure 5:
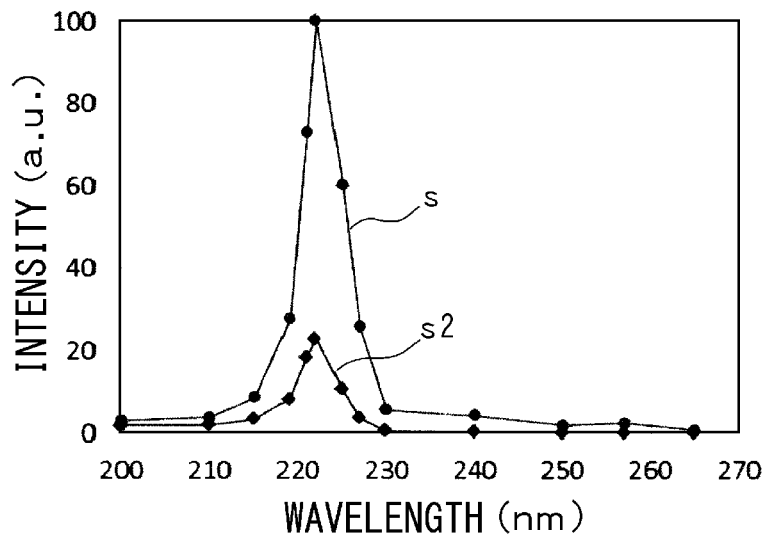
FIG. 5 is a graph illustrating the spectral intensity distribution of the light emitted from the KrCl excimer lamp and a spectral intensity distribution of transmitted light when the light emitted from the KrCl excimer lamp is transmitted through an optical filter (2).

FIG. 4 illustrates the spectral intensity distribution of the light emitted from the KrCl excimer lamp and the spectral intensity distribution of the transmitted light when the light emitted from the KrCl excimer lamp is transmitted through the optical filter (1). FIG. 5 illustrates the spectral intensity distribution of the light emitted from the KrCl excimer lamp and the spectral intensity distribution of the transmitted light when the light emitted from the KrCl excimer lamp is transmitted through the optical filter (2). In FIGS. 4 and 5, the horizontal axis is the wavelength, and the vertical axis is the relative value of the spectral intensity with the spectral intensity at a wavelength of 222 nm as 100. s represents the spectral intensity distribution of the light emitted from the KrCl excimer lamp. s1 represents the spectral intensity distribution of the transmitted light when the light emitted from the KrCl excimer lamp is transmitted through the optical filter (1). s2 represents the spectral intensity distribution of the transmitted light when the light emitted from the KrCl excimer lamp is transmitted through the optical filter (2).

If the optical filter (1) is used and the irradiation amount of light having a wavelength within the wavelength range of 230 to 300 nm is 9 mJ/cm², the irradiation amount of light having a wavelength within the wavelength range of 190 to 230 nm is given by:

$$9 \text{ mJ/cm}^2 \times (a/b) = 9 \text{ mJ/cm}^2 \times 19.8$$
$$= 178 \text{ mJ/cm}^2.$$

If the optical filter (2) is used and the irradiation amount of light having a wavelength within the wavelength range of 230 to 300 nm is 4 mJ/cm², the irradiation amount of light having a wavelength within the wavelength range of 190 to 230 nm is given by:

$$4 \text{ mJ/cm}^2 \times (a/b) = 49 \text{ mJ/cm}^2 \times 48.9$$
$$= 196 \text{ mJ/cm}^2.$$

If an optical filter having an fb/fa value of 0.577 is used and the irradiation amount of light having a wavelength within the wavelength range of 230 to 300 nm is 9 mJ/cm², the irradiation amount of light having a wavelength within the wavelength range of 190 to 230 nm is determined as follows:

$$a/b = (a_0 \times fa)/(b_0 \times fb)$$
$$= (a_0/b_0)/(fb/fa)$$
$$= 6.41/0.577$$
$$= 11.1$$

$$9 \text{ mJ/cm}^2 \times (a/b) = 9 \text{ mJ/cm}^2 \times 11.1$$
$$= 100 \text{ mJ/cm}^2.$$

If an optical filter having an fb/fa of 0.256 is used and the irradiation amount of light having a wavelength within the wavelength range of 230 to 300 nm is 4 mJ/cm$^2$, the irradiation amount of light having a wavelength within the wavelength range of 190 to 230 nm is determined as follows:

$$a/b = (a_0 \times fa)/(b_0 \times fb)$$
$$= (a_0/b_0)/(fb/fa)$$
$$= 6.41/0.256$$
$$= 25.0$$

$$4 \text{ mJ/cm}^2 \times (a/b) = 4 \text{ mJ/cm}^2 \times 25.0$$
$$= 100 \text{ mJ/cm}^2.$$

As described above, if the irradiation amount of light having a wavelength within the wavelength range of 230 to 300 nm is not more than 9 mJ/cm$^2$, the irradiation amount of light having a wavelength within the wavelength range of 190 to 230 nm can be set to not less than 100 mJ/cm$^2$ by using an optical filter 40 having performance satisfying expression (3).

If the irradiation amount of light having a wavelength within the wavelength range of 230 to 300 nm is not more than 4 mJ/cm$^2$, the irradiation amount of light having a wavelength within the wavelength range of 190 to 230 nm can be set to not less than 100 mJ/cm$^2$ by using an optical filter 40 having performance satisfying expression (4).

As a reference example, an optical filter (3) having an fb value of 0 was fabricated. This optical filter (3) had an fa value of 0.123.

Figure 6:
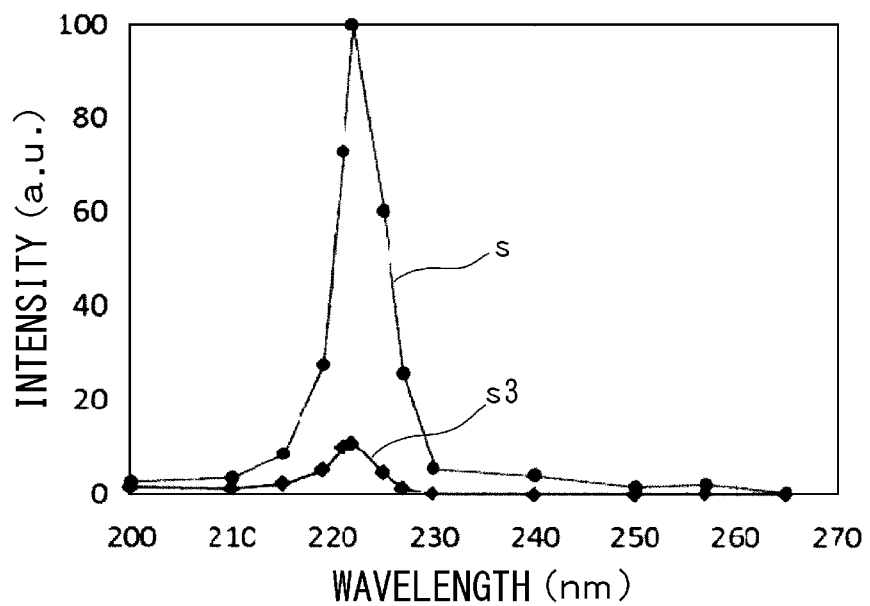
FIG. 6 is a graph illustrating the spectral intensity distribution of the light emitted from the KrCl excimer lamp and a spectral intensity distribution of transmitted light when the light emitted from the KrCl excimer lamp is transmitted through an optical filter (3).

FIG. 6 illustrates the spectral intensity distribution of the light emitted from the KrCl excimer lamp and the spectral intensity distribution of transmitted light when the light emitted from the KrCl excimer lamp is transmitted through the optical filter (3). In FIG. 6, the horizontal axis is the wavelength, and the vertical axis is the relative value of the spectral intensity with the spectral intensity at a wavelength of 222 nm as 100. s represents the spectral intensity distribution of the light emitted from the KrCl excimer lamp. s3 represents the spectral intensity distribution of the transmitted light when the light emitted from the KrCl excimer lamp is transmitted through the optical filter (3).

If the optical filter (1) is used, the irradiation amount of light having a wavelength within the wavelength range of 190 to 230 nm can be set to not less than 100 mJ/cm$^2$ by controlling the power supplied from the power supply unit 30 so that the irradiation amount without the use of the optical filter is not less than 100/fa=100/0.447=224 mJ/cm$^2$.

If the optical filter (2) is used, the irradiation amount of light having a wavelength within the wavelength range of 190 to 230 nm can be set to not less than 100 mJ/cm$^2$ by controlling the power supplied from the power supply unit 30 so that the irradiation amount without the use of the optical filter is not less than 100/fa=100/0.229=437 mJ/cm$^2$.

If the optical filter (3) is used, to set the irradiation amount of light having a wavelength within the wavelength range of 190 to 230 nm to not less than 100 mJ/cm$^2$, power needs to be supplied from the power supply unit 30 so that the irradiation amount without the use of the optical filter is not less than 100/fa=100/0.123=813 mJ/cm$^2$.

As described above, if the optical filter (1) or the optical filter (2) is used as the optical filter 40, the electric energy supplied from the power supply unit 30 to the excimer lamp 20 can be reduced, compared to a case where the optical filter (3) is used.

Next, a case where a KrBr excimer lamp is used as the excimer lamp 20 will be described.

The ratio ($a_0/b_0$) between the cumulative spectral intensity ($a_0$) of light having a wavelength within the wavelength range of 190 to 230 nm and the cumulative spectral intensity ($b_0$) of light having a wavelength within the wavelength range of 230 to 300 nm in the light emitted from the KrBr excimer lamp is 3.73.

Then, if an optical filter having an fb/fa value of 0.336 is used and the irradiation amount of light having a wavelength within the wavelength range of 230 to 300 nm is 4 mJ/cm$^2$, the irradiation amount of light having a wavelength within the wavelength range of 190 to 230 nm is determined as follows:

$$a/b = (a_0 \times fa)/(b_0 \times fb)$$
$$= (a_0/b_0)/(fb/fa)$$
$$= 3.73/0.336$$
$$= 11.1$$

$$9 \text{ mJ/cm}^2 \times (a/b) = 9 \text{ mJ/cm}^2 \times 11.1$$
$$= 100 \text{ mJ/cm}^2.$$

If an optical filter having an fb/fa value of 0.149 is used and the irradiation amount of light having a wavelength within the wavelength range of 230 to 300 nm is 4 mJ/cm$^2$, the irradiation amount of light having a wavelength within the wavelength range of 190 to 230 nm is determined as follows:

$$a/b = (a_0 \times fa)/(b_0 \times fb)$$
$$= (a_0/b_0)/(fb/fa)$$
$$= 3.73/0.149$$
$$= 25.0$$

$$4 \text{ mJ/cm}^2 \times (a/b) = 4 \text{ mJ/cm}^2 \times 25.0$$
$$= 100 \text{ mJ/cm}^2.$$

As described above, if the irradiation amount of light having a wavelength within the wavelength range of 230 to 300 nm is not more than 9 mJ/cm$^2$, the irradiation amount of light having a wavelength within the wavelength range of 190 to 230 nm can be set to not less than 100 mJ/cm$^2$ by using an optical filter 40 having performance satisfying expression (5).

If the irradiation amount of light having a wavelength within the wavelength range of 230 to 300 nm is not more than 4 mJ/cm$^2$, the irradiation amount of light having a wavelength within the wavelength range of 190 to 230 nm can be set to not less than 100 mJ/cm$^2$ by using an optical filter 40 having performance satisfying expression (6).

In the foregoing description, the wavelength range of 190 to 230 nm refers to a wavelength range of 190 nm≤λ≤230 nm, where λ is the wavelength.

The wavelength range of 230 to 300 nm refers to a wavelength range of 230 nm≤λ≤300 nm, where λ is the wavelength.

In the sterilization apparatus according to the present invention, an optical filter 40 having performance satisfying the following expression (7) may preferably be used:

$$0 < fb/fa < (x/100) \times (a_0/b_0), \qquad \text{Exp. (7)}$$

where $a_0$ is the cumulative spectral intensity of light having wavelengths within the wavelength range of 190 to 230 nm and $b_0$ is the cumulative spectral intensity of light having wavelengths within the wavelength range of 230 to 300 nm in the light emitted from the light source, a is the cumulative spectral intensity of light having wavelengths within the wavelength range of 190 to 230 nm and b is the cumulative spectral intensity of light having wavelengths within the wavelength range of 230 to 300 nm in the transmitted light when the light emitted from the light source is transmitted through the optical filter 40, $fa = a/a_0$, $fb = b/b_0$, and x is the irradiation amount of light having a wavelength within the wavelength range of 230 to 300 nm.

If the power supply unit 30 is controlled so that the irradiation amount of light having a wavelength within the wavelength range of 230 to 300 nm in one light irradiation is not more than 9 mJ/cm², the value of x in the foregoing expression (7) is 0<x≤9. If the power supply unit 30 is controlled so that the irradiation amount of light having a wavelength within the wavelength range of 230 to 300 nm is not more than 4 mJ/cm², the value of x is 0<x≤4.

By using an optical filter 40 satisfying such a condition, the irradiation amount of light having a wavelength within the wavelength range of 190 to 230 nm can be set to not less than 100 mJ/cm² while the irradiation amount of light having a wavelength within the wavelength range of 230 to 300 nm is suppressed to not more than 9 mJ/cm² or not more than 4 mJ/cm².

As described above, according to the sterilization apparatus of the present invention, the power supply unit 30 is controlled by the control unit 35 so that the irradiation amount of light having a wavelength within the wavelength range of 230 to 300 nm in one light irradiation is not more than 9 mJ/cm², whereby sterilization target organisms present on the body or in the body can be killed or inactivated while damage to human cells is suppressed.

Since the optical filter 40 does not need to fully cut off the light having a wavelength within the wavelength range 230 to 300 nm, an optical filter 40 highly transparent to light having a wavelength within the wavelength range of 190 to 230 nm can be used. Since high power therefore does not need to be supplied to the excimer lamp 20, high energy efficiency is obtained.

While the embodiment of the sterilization apparatus according to the present invention has been described above, the present invention is not limited to the foregoing embodiment, and various modifications may be made thereto.

For example, the light source is not limited to an excimer lamp, and an LED using a nitride semiconductor, such as AlGaN and AlN, may be used as long as the emitted light has wavelengths within the wavelength range of 190 nm to 230 nm and the wavelength range of 230 to 300 nm.

The optical filter is not limited to one that includes a dielectric multilayer film including $SiO_2$ films and $MgF_2$ films. Optical filters that include other dielectric multilayer films may be used.

REFERENCE SIGNS LIST 10 casing
11 ultraviolet transmission window portion
15 reflecting mirror
20 excimer lamp
21 discharge container
22 one wall member
22a outer peripheral surface
23 other wall member
23a outer surface
24, 25 sealing wall portion
26 one electrode
27 other electrode
28 light emitting element replenishment material
30 power supply unit
35 control unit
40 optical filter
41 fixing member
P sterilization target portion
S discharge space

The invention claimed is:

1. A sterilization apparatus configured to irradiate a sterilization target organism on a body or in the body with light and thereby killing or inactivating the sterilization target organism, the sterilization apparatus including:
   an optical filter;
   a light source configured to emit light through the optical filter, the light having wavelengths within a wavelength range of 190 nm to 230 nm and a wavelength range of 230 to 300 nm;
   a power supply unit configured to supply power to the light source; and
   a control unit configured to control the power supply unit, wherein
   the power supply unit is controlled by the control unit so that an irradiation amount of light configured to irradiate the sterilization target organism on the body or in the body to thereby kill or inactivate the sterilization target organism has a wavelength within the wavelength range of 230 to 300 nm in one light irradiation and is more than or equal to 4 mJ/cm² and not more than 9 mJ/cm², and an irradiation amount of light having a wavelength within the wavelength range of 190 to 230 nm in one light irradiation is not less than 100 mJ/cm².

2. The sterilization apparatus according to claim 1, wherein the optical filter has performance satisfying the following expression (1):

$$0 < fb/fa < 0.09 \times (a_0/b_0), \qquad \text{Exp. (1):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, $fa = a/a_0$, and $fb = b/b_0$.

3. The sterilization apparatus according to claim 1, wherein the power supply unit is controlled by the control unit so that the irradiation amount of light having a wavelength within the wavelength range of 230 to 300 nm in one light irradiation is not more than 4 mJ/cm$^2$.

4. The sterilization apparatus according to claim 3, wherein the optical filter has performance satisfying the following expression (2):

$$0 < fb/fa < 0.04 \times (a_0/b_0), \quad \text{Exp. (2):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

5. The sterilization apparatus according to claim 1, wherein
the light source is a KrCl excimer lamp, and
the optical filter has performance satisfying the following expression (3):

$$0 < fb/fa < 0.577, \quad \text{Exp. (3):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

6. The sterilization apparatus according to claim 3, wherein
the light source is a KrCl excimer lamp, and
the optical filter has performance satisfying the following expression (4):

$$0 < fb/fa < 0.256, \quad \text{Exp. (4):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

7. The sterilization apparatus according to claim 1, wherein
the light source is a KrBr excimer lamp, and
the optical filter has performance satisfying the following expression (5):

$$0 < fb/fa < 0.336, \quad \text{Exp. (5):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

8. The sterilization apparatus according to claim 3, wherein
the light source is a KrBr excimer lamp, and
the optical filter has performance satisfying the following expression (6):

$$0 < fb/fa < 0.149, \quad \text{Exp. (6):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, and fb=b/$b_0$.

9. The sterilization apparatus according to claim 1, wherein the optical filter has performance satisfying the following expression (7):

$$0 < fb/fa < (x/100) \times (a_0/b_0), \quad \text{Exp. (7):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, fa=a/$a_0$, fb=b/$b_0$, and x is the irradiation amount of light having a wavelength within the wavelength range of 230 to 300 nm.

10. The sterilization apparatus according to claim 1, wherein the light source is an LED using a nitride semiconductor.

11. The sterilization apparatus according to claim 1, wherein the optical filter includes a dielectric multilayer film including an SiO$_2$ film and an MgF$_2$ film.

12. The sterilization apparatus according to claim 3, wherein the optical filter has performance satisfying the following expression (7):

$$0 < fb/fa < (x/100) \times (a_0/b_0), \quad \text{Exp. (7):}$$

where $a_0$ is a cumulative spectral intensity of light having wavelengths within the wavelength range of 190 to 230 nm and $b_0$ is a cumulative spectral intensity of light having wavelengths within the wavelength range of 230 to 300 nm in the light emitted from the light source, a is a cumulative spectral intensity of light having wavelengths within the wavelength range of 190 to 230 nm and b is a cumulative spectral intensity of light having wavelengths within the wavelength range of 230 to 300 nm in transmitted light when the light emitted from the light source is transmitted through the optical filter, $f_a=a/a_0$, $f_b=b/b_0$, and x is the irradiation amount of light having a wavelength within the wavelength range of 230 to 300 nm.

13. The sterilization apparatus according to claim 3, wherein the light source is an LED using a nitride semiconductor.

14. The sterilization apparatus according to claim 3, wherein the optical filter includes a dielectric multilayer film including an $SiO_2$ film and an $MgF_2$ film.

15. A sterilization apparatus configured to irradiate a sterilization target organism on a body or in the body with light and thereby killing or inactivating the sterilization target organism, the sterilization apparatus including:
   an optical filter;
   a light source configured to emit light through the optical filter, the light having wavelengths within a wavelength range of 190 nm to 230 nm and within a wavelength range of 230 nm to 300 nm;
   a power supply unit configured to supply power to the light source; and
   a control unit configured to control the power supply unit, wherein
   the power supply unit is controlled by the control unit so that an irradiation amount of light configured to irradiate the sterilization target organism on the body or in the body with light and thereby killing or inactivating the sterilization target organism has a wavelength within the wavelength range of 230 to 300 nm in one light irradiation is set to a value in a range from about 4 $mJ/cm^2$ to 9 $mJ/cm^2$, and an irradiation amount of light having a wavelength within the wavelength range of 190 to 230 nm in one light irradiation is set to a minimum value.

16. The sterilization apparatus according to claim 15, wherein the minimum value is 100 $mJ/cm^2$.

17. A sterilization apparatus configured to irradiate a sterilization target organism on a body or in the body with light and thereby killing or inactivating the sterilization target organism, the sterilization apparatus including:
   an optical filter;
   a light source configured to emit light through the optical filter, the light having wavelengths in a first wavelength range of greater than 190 nm to less than 230 nm and wavelengths in a second wavelength range of more than 230 nm to less than 300 nm;
   a power supply unit configured to supply power to the light source; and
   a control unit configured to control the power supply unit, wherein
   the power supply unit is controlled by the control unit so that an irradiation amount of light configured to irradiate the sterilization target organism on a body or in the body with light and thereby killing or inactivating the sterilization target organism in the first wavelength range in one light irradiation is set to a first value, and an irradiation amount of light configured to irradiate a sterilization target organism on a body or in the body with light and thereby killing or inactivating the sterilization target organism in the second wavelength range in one light irradiation is simultaneously set to a second value in a range from 4.0 $mJ/cm^2$ to 9 $mJ/cm^2$, and the first value is greater than the second value.

18. The sterilization apparatus according to claim 17, wherein the second value is a set to be less than a human minimal erythema dose (MED).

19. The sterilization apparatus according to claim 17, wherein the light emitted in the first wavelength range increases in spectral intensity to a peak value with a decrease in wavelength from 230 nm, and light emitted in the second wavelength range decreases in spectral intensity with an increase in wavelength from 230 nm over at least a portion of the wavelength range of more than 230 nm to less than 300 nm.

* * * * *